(12) United States Patent
McCormack et al.

(10) Patent No.: US 7,906,669 B2
(45) Date of Patent: *Mar. 15, 2011

(54) METALLOCENE-BASED PHOSPHORUS CHIRAL PHOSPHINES

(75) Inventors: Peter McCormack, Merseyside (GB); Chen Weiping, Liverpool (GB); John Whittall, Lancaster (GB)

(73) Assignee: Solvias AG, Basel (CH)

( * ) Notice: Subject to any disclaimer, the term of this patent is extended or adjusted under 35 U.S.C. 154(b) by 228 days.

This patent is subject to a terminal disclaimer.

(21) Appl. No.: 11/813,987

(22) PCT Filed: Jan. 13, 2006

(86) PCT No.: PCT/GB2006/000114

§ 371 (c)(1),
(2), (4) Date: Jun. 11, 2008

(87) PCT Pub. No.: WO2006/075166

PCT Pub. Date: Jul. 20, 2006

(65) Prior Publication Data

US 2009/0137824 A1    May 28, 2009

(30) Foreign Application Priority Data

Jan. 14, 2005 (GB) ................... 0500702.6

(51) Int. Cl.
C08F 17/02 (2006.01)
C07F 15/00 (2006.01)
C07F 9/02 (2006.01)
C07F 9/50 (2006.01)

(52) U.S. Cl. ........ 556/143; 556/138; 556/140; 556/136; 556/22; 556/21; 556/20; 556/19; 556/18; 556/13

(58) Field of Classification Search .................. 556/138, 556/143, 144, 22
See application file for complete search history.

(56) References Cited

U.S. PATENT DOCUMENTS

2008/0281106 A1* 11/2008 Chen et al. .................... 548/101

FOREIGN PATENT DOCUMENTS

JP      2005041847 A    2/2005
WO    WO 2005/068477 A1    7/2005
WO    WO 2005/068478 A1 *  7/2005

OTHER PUBLICATIONS

Oohara et al. (Tetrahedron: Asymmetry, 2003, 14, 2171-2175).*
Drahoňovsky et al. (Collect. Czech. Chem. Commun., 2001, 66, 588-604).*
Guillaneux, et al. 2000. Diferrocenylphosphine: A facile synthesis and its use to prepare chiral phosphines. *Collect. Czech. Chem. Commun.*, 65:717-728.

Houpis, et al. 2005. Synthesis of PPAR agonist via asymmetric hydrogenation of a cinnamic acid derivative and stereospecific Displacement of (S)-2-chloropropionic acid. *Organic Letters*, 7(10):1947-1950.

(Continued)

*Primary Examiner* — Rip A. Lee
(74) *Attorney, Agent, or Firm* — Wenderoth, Lind & Ponack, L.L.P.

(57) ABSTRACT

The present invention concerns a metallocene-based phosphine ligand for use in enantioselective catalysis, the ligand having the Formula (I): Wherein M is a metal; Z is P or As; L is a suitable linker; $R^1$ is selected from alkyl, alkoxy, alkylamino, cycloalkyl, cycloalkoxy, cycloalkylamino carbocyclic aryl, substituted and unsubstituted carbocyclic aryloxy, heteroaryl, heteroaryloxy, carbocyclic arylamino and heteroarylamino; X* is selected from (II): Wherein R, $R^2$ and $R^3$ are independently selected from optionally substituted branched- and straight-chain alkyl, cycloalkyl, heterocycloalkyl, carbocyclic aryl, and heteroaryl.

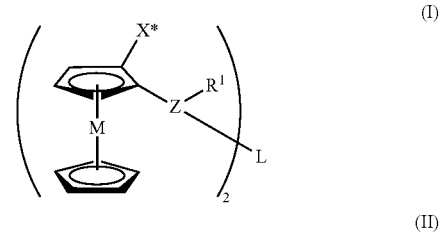

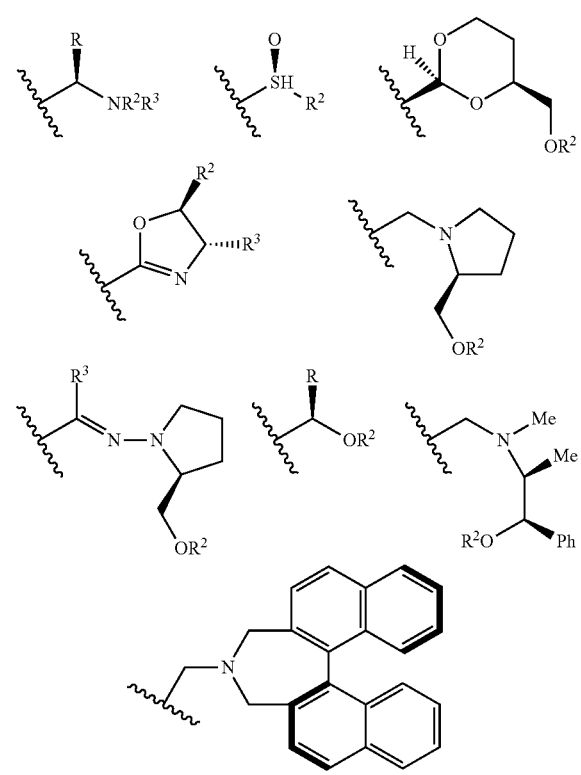

14 Claims, No Drawings

OTHER PUBLICATIONS

Kim, et al. 1994. Synthesis and reaction chemistry of some ferrocene-containing chelate ligands with dirhodium acetate: X-ray crystal structure of $(\eta^1\text{-}(S,R)\text{-CPFA})_2\text{Rh}_2(\text{OAc})_4$. *Bull. Korean Chem. Soc.*, 15(11):990-996.

Oohara, et al. 2003. A novel P-chirogenic phosphine ligand, (*S,S*)-1,2,-bis-[(ferrocenyl)methylphosphino]ethane; synthesis and use in rhodium-catalyzed asymmetric hydrogenation and palladium-catalyzed asymmetric allyic alkylation. *Tetrahedron: Asymmetry*, 14:2171-2175.

International Search Report for Application No. GB0500702.6, dated Apr. 22, 2005.

International Search Report for Application No. GB0600713.2, dated May 26, 2006.

International Preliminary Report on Patentability and Written Opinion of the International Searching Authority for PCT/GB2006/000114, dated Jul. 17, 2007.

* cited by examiner

METALLOCENE-BASED PHOSPHORUS CHIRAL PHOSPHINES

CROSS REFERENCE TO RELATED APPLICATION

This application claims the benefit and priority to and is a U.S. National Phase of PCT International Application Number PCT/GB2006/000114, filed on Jan. 13, 2006, designating the United States of America, which claims priority under 35 U.S.C. §119 to British Application Number 0500702.6 filed on Jan. 14, 2005. The disclosures of the above-described applications are hereby incorporated by reference in their entirety.

This invention relates to novel chiral metallocene-based phosphine ligands and methods for their preparation. In addition, this invention relates to metal-ligand complexes that can be used as catalysts or precatalysts for asymmetric transformation reactions to generate products of high enantiomeric excess. Similarly structured arsines are also within the scope of this invention.

Certain known diphosphine ligands exhibit chirality only at the phosphorus atoms:

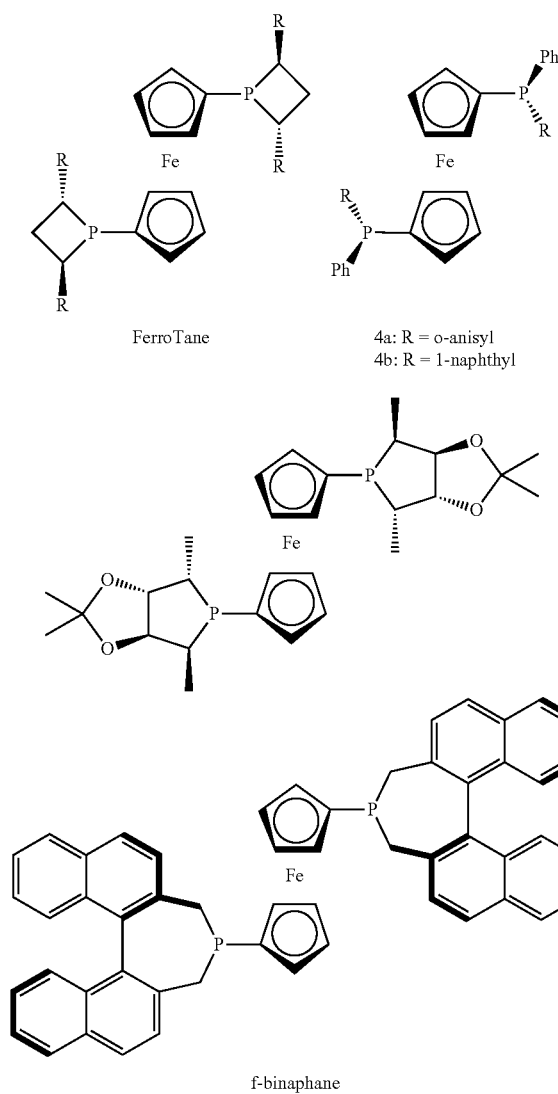

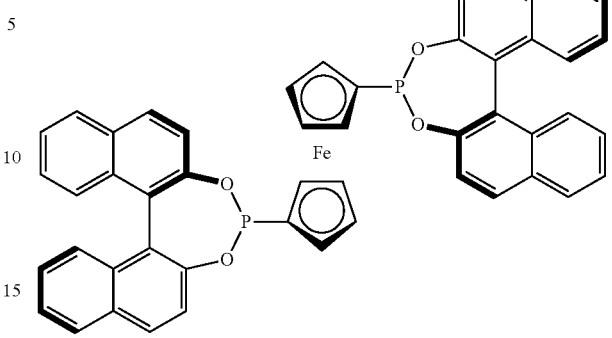

The synthesis of chiral 1,1'-bis(phosphetano) ferrocenes (FerroTANE) has been independently reported by Marinetti[15] and Burk[16]. FerroTANE has been successfully applied in Rh-catalyzed hydrogenation of itaconates and (E)-β-(acylamino)acrylates[17].

Mezzetti[18] and van Leeuwen[19] have independently reported P-chiral ferrocenyl bisphosphines 4a and 4b. These two ligands have shown excellent enantioselectivities (up to 99% ee) for asymmetric hydrogenation of α-dehydroamino acid derivatives.

Zhang has reported a 1,1'-bis(Phospholanyl)ferrocene ligand 5 with ketal substitutes at the 3 and 4 positions.[20] The ligand has shown excellent enantioselectivities in hydrogenation of β-dehydroamino acid derivatives. The ketal groups of the ligand are important for achieving the high enantioselectivity, since the corresponding ligand without ketal groups only provides moderate ee's. Zhang has also developed a 1,1'-bis(dinaphthophosphepinyl)ferrocene ligand, f-binaphane, which has been successfully applied in the Ir-catalyzed hydrogenation of acyclic aryl imines.[21]

Reetz has developed a binaphthol-derived ferrocene-based bisphosphonite ligand 6[22], which has shown excellent reactivities and enantioselectivities in Rh-catalyzed hydrogenation of itaconates and α-dehydroamino acid derivatives.

Another class of known ligands exhibits both planar and phosphorus chirality:

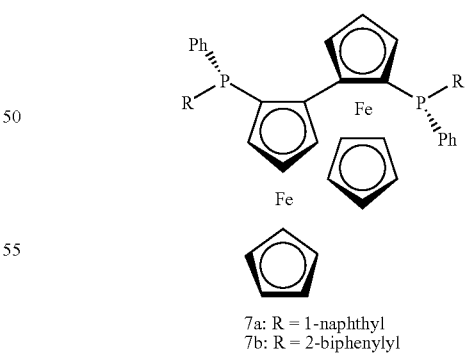

7a: R = 1-naphthyl
7b: R = 2-biphenylyl

Van Leeuwen has reported ferrocene-based bisphosphines combining planar and phosphorus chirality 7a and 7b[23]. These two ligands have shown excellent enantioselectivities (up to 99% ee) for asymmetric allylic alkylations.

More recently, Togni reported the first tridentate ferrocene-based phosphine ligand 12 combining planar, phosphorus and carbon chirality.[24]

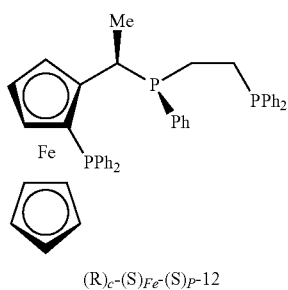

(R)$_c$-(S)$_{Fe}$-(S)$_P$-12

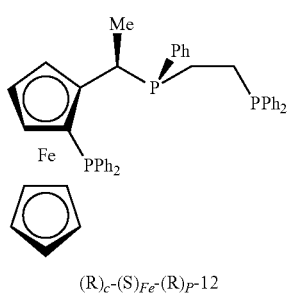

(R)$_c$-(S)$_{Fe}$-(R)$_P$-12

We have previously reported novel classes of chiral phosphine and arsine ligands, and processes for their preparation, and these are reported in co-pending applications published under WO-A-2005/068477 and WO-A-2005/068478.

It would be advantageous to design improved chiral bisphosphine ligands for use in enantioselective catalysis.

According to the present invention there is provided a metallocene-based phosphine or arsine ligand for use in enantioselective catalysis, the ligand having the Formula:

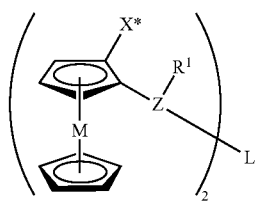

Wherein:

M is a metal;

Z is P or Ar;

L is a suitable linker;

R$^1$ is selected from substituted and unsubstituted, branched- and straight-chain alkyl, alkoxy, alkylamino, substituted and unsubstituted cycloalkyl, substituted and unsubstituted cycloalkoxy, substituted and unsubstituted cycloalkylamino, substituted and unsubstituted carbocyclic aryl, substituted and unsubstituted carbocyclic aryloxy, substituted and unsubstituted heteroaryl, substituted and unsubstituted heteroaryloxy, substituted and unsubstituted carbocyclic arylamino and substituted and unsubstituted heteroarylamino, wherein the or each heteroatom is independently selected from sulphur, nitrogen, and oxygen; and X* is selected from:

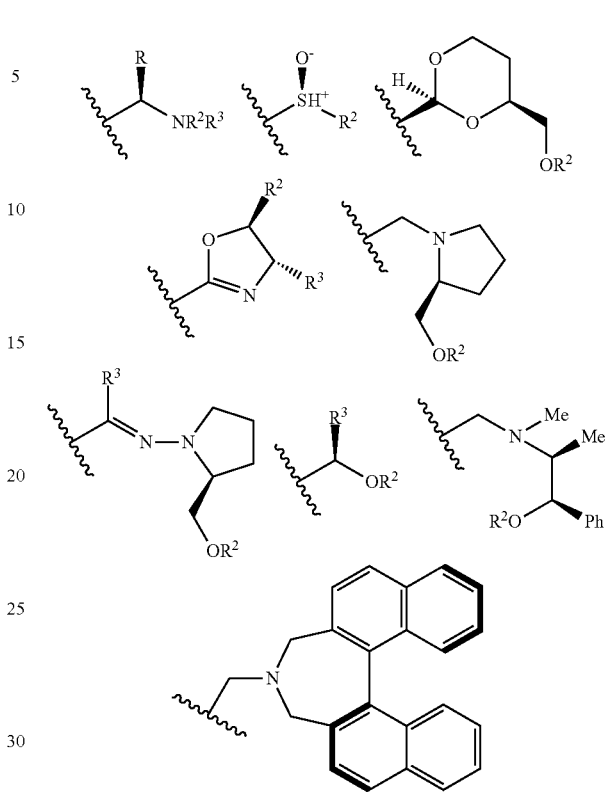

Wherein R, R$^2$ and R$^3$ are independently selected from substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen.

The R$^2$ and R$^3$ groups may be substituted by each other, forming together an optionally substituted hetero-ring system.

Preferably M is Fe, although Ru may be another preferred M.

L preferably comprises a difunctional moiety having the capability at each functionality to bind to phosphorus or arsenic, as the case may be. Generally the linker (L) will be derived from a difunctional compound, in particular a compound having at least two functional groups capable of binding to phosphorus or arsenic, as the case may be. The difunctional compound may conveniently comprise a compound which can be di-lithiated or reacted to form a di-Grignard reagent, or otherwise treated, to form a dianionic reactive species which can then be combined directly with phosphorus or arsenic, in a diastereoselective manner to form a chiral phosphorus or arsenic as the case may be. In this case, a first anionic component of the dianionic reactive species may combine with a phosphorus (or arsenic) substituent in a first ligand precursor of the ligand according to the invention, and a second anionic component of the dianionic reactive species may combine again in a diastereoselective manner with a phosphorus (or arsenic) substituent in a second ligand precursor of the ligand again to form a chiral phosphorus (or arsenic) centre according to the invention (the first and second ligand precursors being the same as each other) to connect the first and second ligand precursors together via the linker. Usually a leaving group such as a halide will be provided on the phosphorus (or arsenic) substituents of the first and second ligand precursors, which leaving group departs on combination of the anionic component with the phosphorus (or arsenic) substituent. The following scheme is illustrative of this process:

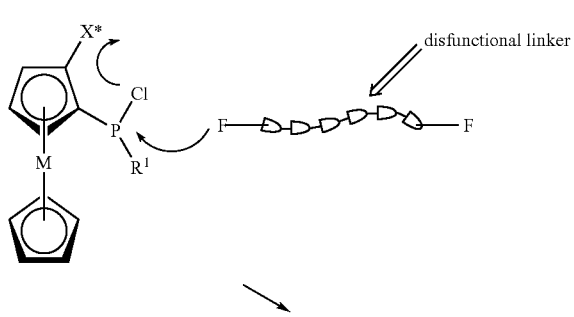
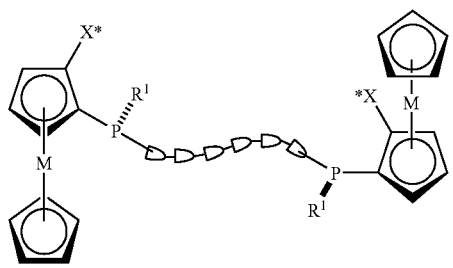
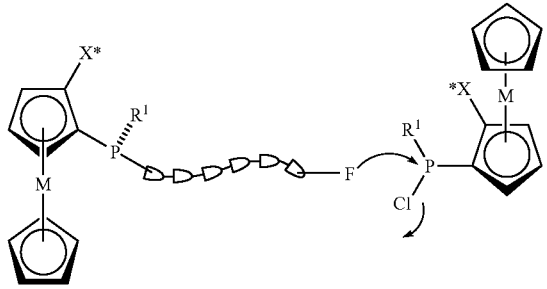

For example, L may be selected from ferrocene and other metallocenes, diphenyl ethers, xanthenes, 2,3-benzothiophene, 1,2-benzene, succinimides, cyclic anhydrides and many others. Conveniently, although not necessarily such dianionic linkers may be made from a corresponding di-halo precursor, e.g.:

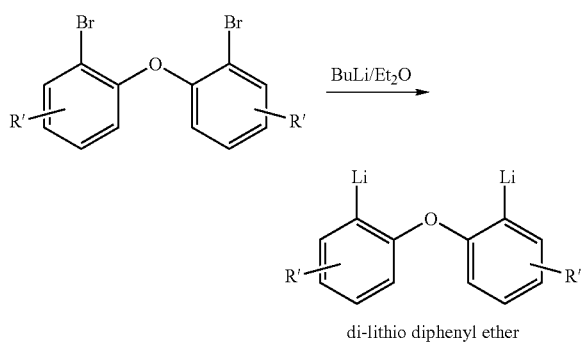

di-lithio diphenyl ether

Wherein R' represents any suitable number of any one or more suitable substituents.

Other suitable dianionic linkers may be represented as follows:

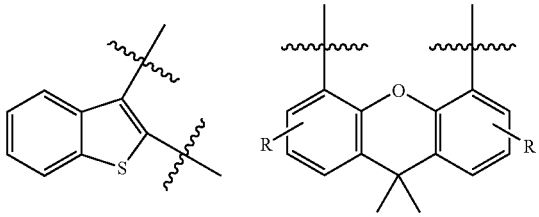

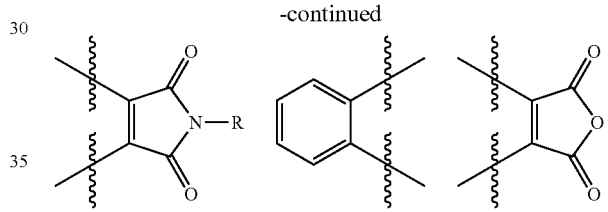

However, ferrocene and other metallocenes may also be selected for use as linkers in accordance with the invention, and there are many other suitable moieties which could also be selected.

Preferred $R^1$ include phenyl, methyl, cyclohexyl and t-butyl groups.

Preferred $R^2$ and $R^3$ include, independently, methyl, ethyl, isopropyl and t-butyl groups. Also, $R^2$ and $R^3$ may form, together with the nitrogen to which they are attached, an optionally substituted hetero-ring such as morpholine, pyrollidine, piperidine, and derivatives thereof.

Certain ligands of the invention are derived from Ugi's amine and one preferred ligand in accordance with the invention (wherein the dianionic linker is ferrocene) may be represented as follows:

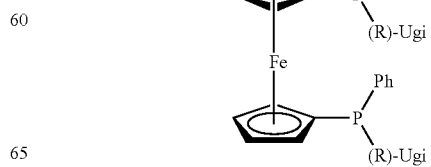

The same preferred ligand, with the Ugi amine groups fully represented may be shown as:

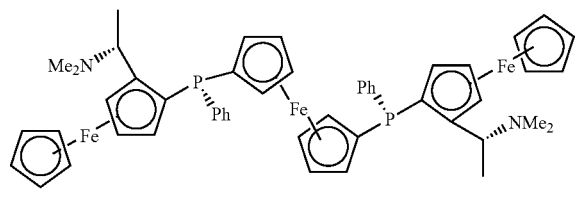

The invention also relates to the enantiomers and diastereomers of the ligands described above.

Ligands in accordance with the invention may also be represented as follows:

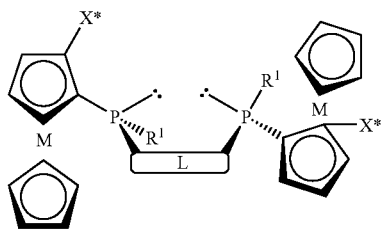

Wherein M, L, R$^1$ and X* are as previously defined, and wherein the phosphorus may if desired be at least partially replaced by arsenic.

The ligand of the invention exhibits chirality at phosphorus (or arsenic). Preferably, the chiral configuration of the phosphorus (or arsenic) substituents at opposite ends of the linker molecule is the same.

Also provided in accordance with the invention is a transition metal complex comprising a transition metal coordinated to the ligand of the invention. The metal is preferably a Group VIb or a Group VIII metal, especially rhodium, ruthenium, iridium, palladium, platinum or nickel.

Synthesis of ferrocene-based phosphorus chiral phosphines in accordance with the invention may be effected in accordance with the following scheme:

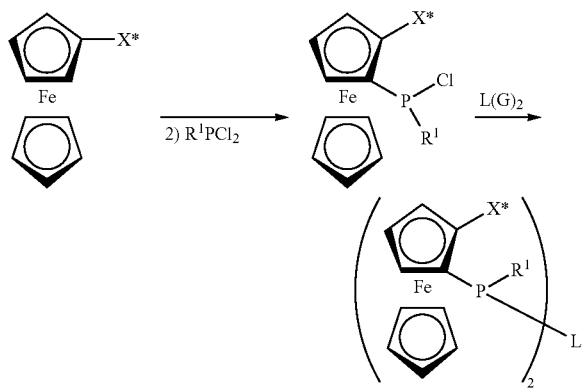

wherein L is a linker derived from an organolithium species or Grignard reagent L(G)$_2$ and wherein X* and R$^1$ are as previously defined. The same synthetic scheme is generally applicable to other chiral metallocene-based ligands in accordance with the invention.

The invention will now be more particularly illustrated with reference to the following Examples.

EXAMPLE 1

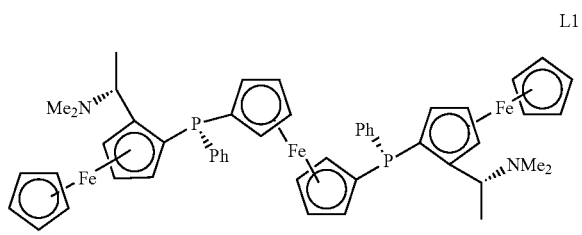

1,1'bis-[(S$_P$,R$_C$,S$_{Fe}$)(1-N,N-Dimethylamino)ethylferrocenyl)phenylphosphino]ferrocene L1

To a solution of (R)—N,N-dimethyl-1-ferrocenylethylamine [(R)-Ugi's amine] (3.09 g, 12 mmol) in Et$_2$O (20 ml) was added 1.5 M t-BuLi solution in pentane (8.0 ml, 12.0 mmol) at −78° C. After addition was completed, the mixture was warmed to room temperature, and stirred for 1.5 h at room temperature. The mixture was then cooled to −78° C. again, and dichlorophenylphosphine (1.63 ml, 12.0 mmol) was added in one portion. After stirring for 20 min at −78° C., the mixture was slowly warmed to room temperature, and stirred for 1.5 h at room temperature. The mixture was then cooled to −78° C. again, and a suspension of 1,1' dilithioferrocene [prepared from 1,1' dibromoferrocene (1.72 g, 5.0 mmol) and 1.5 M t-BuLi solution in pentane (14.0 ml, 21.0 mmol) in Et$_2$O (20 ml) at −78° C.] was added slowly via a cannula. The mixture was warmed to room temperature and allowed to stir for 12 h. The reaction was quenched by the addition of saturated NaHCO$_3$ solution (20 ml). The organic layer was separated and dried over MgSO$_4$ and the solvent removed under reduced pressure. The filtrate was concentrated. The residue was purified by chromatography (SiO$_2$, hexane-EtOAc-Et$_3$N=85:10:5) to afford an orange solid (3.88 g, 85%) as a mixture of 95% bis-(S$_P$,R$_C$,S$_{Fe}$) title compound L1 and 5% (R$_P$,R$_C$,S$_{Fe}$—S$_P$,R$_C$,S$_{Fe}$) meso compound. The meso compound can be removed by further careful purification using chromatography (SiO$_2$, hexane-EtOAc-Et$_3$N=85:10:5). Orange/yellow crystalline solid m.p. 190-192° C. [α]$_D$=−427° (c=0.005 (g/ml), toluene); $^1$H NMR (CDCl$_3$, 400.13 MHz): δ 1.14 (d, 6H, J=6.7 Hz), 1.50 (s, 12H); 3.43 (m, 2H); 3.83 (m, 2H); 3.87 (m, 2H); 4.01 (s, 10H), 4.09 (t, 2H, J=2.4 Hz); 4.11 (m, 2H); 4.20 (m, 2H); 4.28 (m, 2H); 4.61 (m, 2H); 4.42 (d, 2H, J=5.3 Hz); 7.18 (m, 6H); 7.42 (m, 4H) ppm. $^{13}$C NMR (CDCl$_3$, 100.61 MHz): δ 38.28, 57.40 (d, J=5.6 Hz); 67.02, 69.04 (d, J=4.0 Hz); 69.16 (d, J=51.6 Hz); 69.66, 71.60 (d, J=4.8 Hz), 71.91 (d, J=7.2 Hz), 72.18 (d, J=5.6 Hz), 75.96 (d, J=35.7 Hz), 79.96 (d, J=6.4 Hz), 95.73 (d, J=19.1 Hz), 127.32 (d, J=7.9 Hz), 127.62, 133.12 (d, J=21.4 Hz), 139.73 (d, J=4.0 Hz). $^{31}$P NMR (CDCl$_3$, 162 MHz): δ-34.88 (s). Found: C, 65.53; H, 5.92; N, 3.01 Calculated for C$_{50}$H$_{54}$Fe$_3$N$_2$P$_2$; C, 65.81; H, 5.97; N, 3.07. HRMS (10 eV, ES+): Calcd for C$_{50}$H$_{55}$Fe$_3$N$_2$P$_2$ [M+H]$^+$: 913.1889; Found: 913.1952.

The label S$_P$ refers to S configuration at phosphorus, R$_C$ refers to R configuration at carbon (or other auxiliary) and S$_{Fe}$ refers to S configuration at the planar chiral element.

Note: To maintain consistency in all of this work when assigning configuration at phosphorus we have given the Ugi amine(1-N,N-dimethylamino)ethylferrocenyl) fragment a priority of 1, the incoming lithium or Grignard nucleophile (in the above example lithioferrocene) a priority of 2 and the remaining group a priority of 3. This method will not always be consistent with the rigorous approach. These assignations and the proposed phosphorus configurations have been checked using single crystal x-ray crystallography.

EXAMPLE 2

2,2'bis-[($S_P$,$R_C$,$S_{Fe}$)(1-N,N-Dimethylamino)ethylferrocenyl)phenylphosphino]-4-tolylether L2

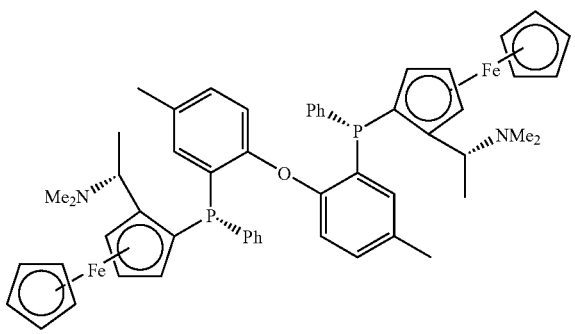

L2

Using a similar procedure to that described above with the exception that a suspension of 2,2' dilithio-4-tolylether [prepared by known procedures from 2,2' dibromo-4-tolylether (1.78 g, 5.0 mmol) and 1.5 M t-BuLi solution in pentane (14.0 ml, 21.0 mmol) in Et$_2$O (20 ml) at −78° C.] was used as the linker reagent rather than 1,1' dilithioferrocene.

Yellow crystalline solid [α]$_D$=−105° (c=0.005 (g/ml), toluene); $^1$H NMR (CDCl$_3$, 400.13 MHz): δ 1.23 (d, 6H), 1.72 (s, 12H); 2.28 (s, 6H); 4.11 (s, 10H); 4.12 (m, 2H overlapping); 4.28 (m, 2H); 4.31 (m, 4H); 4.35 (m, 2H, overlapping); 7.00-7.30 (m, 14H) ppm. $^{31}$P NMR (CDCl$_3$, 162 MHz): δ-40.69 (br s) ppm.

EXAMPLE 3

2,7-di-tert-butyl-4,5-bis-[($S_P$,$R_C$,$S_{Fe}$)(1-N,N-Dimethylamino)ethylferrocenyl)phenylphosphino]-9,9-dimethyl-9H-xanthene

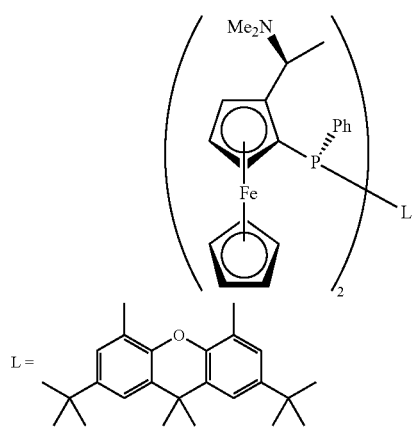

L3

Using a similar procedure to that described above with the exception that a suspension of 2,7-di-tert-butyl-4,5-dilithio-9,9-dimethyl-9H-xanthene [prepared by known procedures from 2,7-di-tert-butyl-4,5-dibromo-9,9-dimethyl-9H-xanthene and 1.5 M t-BuLi solution in pentane in Et$_2$O at −78° C.] was used as the linker reagent rather than 1,1' dilithioferrocene.

Orange/yellow crystalline solid; $^1$H NMR (CDCl$_3$, 400.13 MHz): δ 1.12 (s, 18H); 1.13 (m, 6 H overlapping); 1.78 (s, 6H); 1.98 (s, 12H); 3.99 (m, 2H); 4.15 (s, 10H overlapping); 4.32 (m, 2H); 4.41 (m, 4H); 7.00-7.40 (m, 14H) ppm. $^{31}$P NMR (CDCl$_3$, 162 MHz): δ−41.78 (br s) ppm. HRMS (10 eV, ES+): Calcd for C$_{63}$H$_{75}$Fe$_2$N$_2$OP$_2$ [M+H]$^+$: 1049.4053; Found: 1049.4222

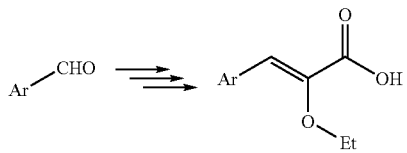

Scheme 1.0 Route for the Synthesis of Substrates of Formula (VI)

EXAMPLE 4

(Z)-2-Ethoxy-3-(thiophen-3-yl)acrylic Acid

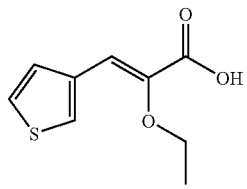

Following the procedure of (Vol. 8, No. 6, 2004, Organic Research & Development) with modification, this compound was synthesised as follows: Ethyl chloroacetate (44.8 ml, 421 mmol) and anhydrous ethanol (30 ml) were cooled to 10-12° C. A solution of sodium ethoxide in ethanol (21% w/w, 165 ml) was added over 25 min at 12-16° C. under N$_2$. After addition was complete the reaction mixture was warmed to 25° C. and stirred for 1 h. The mixture was then cooled to 10° C. and solid NaOEt (33.3 g, 488 mmol) was then added portion-wise over 0.5 h at 10-14° C. Ethanol (20 ml) was then added followed by the addition of diethyl carbonate (31 ml, 256 mmol). The slurry was then cooled to 0-5° C. and then 3-thiophene carboxaldehyde (20.2 g, 179.5 mmol) was added over a period of 1 h. After addition was complete the mixture was stirred at 40° C. in an oil bath for 15 h. The slurry was then cooled to 10-15° C. and then water (40 ml) was added followed by the addition of aqueous NaOH (55 ml of a 10 M solution). The resulting slurry was then stirred at pH 14 for 3 h at 20° C. The mixture was then diluted with water (60 ml) and then placed under reduced pressure at 45° C. to remove most of the ethanol and some water. The resulting thick slurry was then cooled to 4° C. in an ice-bath and then treated with conc. HCl (115 ml) drop-wise. The resulting slurry was then stirred at room temperature for 1.5 h and then extracted with EtOAc (2×200 ml) and the organic layer washed with water, brine and then dried (sodium sulphate). Evaporation of the solvent under reduced pressure afforded a deep-brown residue. This was dissolved in 5 M NaOH (250 ml) and this solution was washed with EtOAc (100 ml). The basic aqueous was then cooled to 4° C. and acidified with conc. HCl (11 M) to pH 4-6. The product was extracted with diethyl ether (3×200 ml), washed with brine, dried (sodium sulphate) and the solvent removed under reduced pressure. The residue was then filtered through a pad of silica (eluent hexane:EtOAc 90:10). The solvent was removed under reduced pressure and then the residue recrystallised from Et$_2$O/hexane to afford the title compound as yellow crystals (79%). M.p. 88-89° C. $^1$H NMR (CDCl$_3$, 250 MHz) δ 11.16 (1H, br s, COOH), 7.73-7.75 (1H, dd, j=0.5 Hz, Ar), 7.44-7.47 (1H, dd, J=1 Hz, Ar), 7.25-7.28 (1H, m, Ar), 7.18 (1H, s, CH═C), 3.96-4.05 (2H, q, J=7 Hz, CH$_2$CH$_3$), 1.35 (3H, t, J=7 Hz, CH$_2$CH$_3$),). Found: C, 54.64; H, 5.08; Calculated for C$_9$H$_{10}$SO$_3$ C, 54.54; H, 5.08. M/z [(Cl) 222 (M)$^+$ 30%, 223 (M+H)+ 50%, 240 (M+NH$_4$)$^+$ 100%; Found: 223.09705; required for C$_{12}$H15O$_4$ 223.09155]. M/z [(Cl) 198 (M)$^+$ 22%, 199 (M+H)$^+$ 50%, 216 (M+NH$_4$)$^+$ 100%].

Using a similar procedure to that described above the following compounds were prepared:

EXAMPLE 5

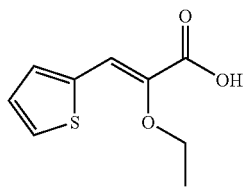

(Z)-2-ethoxy-3-(thiophen-2-yl)acrylic Acid

Pink crystalline solid (77%). M.p. 103-104° C. $^1$H NMR (CDCl$_3$, 250 MHz) δ 12.15 (1H, br s, COOH), 7.48 (1H, s CH═C), 7.40 (1H, m, Ar), 7.29 ((1H, m, Ar), 7.08 (1H, m, Ar), 4.11 (2H, q, J=7 Hz, CH$_2$CH$_3$), 1.48 (3H, t, J=7 Hz, CH$_2$CH$_3$). Found: C, 54.82; H, 5.11, S, 16.00 Calculated for C$_9$H$_{10}$SO$_3$ C, 54.54; H, 5.08; S, 16.16]. M/z [(Cl) 222 (M)$^+$ 30%, 223 (M+H)+ 50%, 240 (M+NH$_4$)$^+$ 100%; Found: 223.09705; required for C$_{12}$H15O$_4$ 223.09155. M/z [(Cl) 198 (M)$^+$ 22%, 199 (M+H)$^+$ 50%, 216 (M+NH$_4$)$^+$ 100%].

EXAMPLE 6

(Z)-3-(4-Cyanophenyl)-2-ethoxy Acrylic Acid

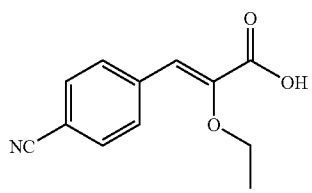

White crystalline solid M.p. 171-172° C. $^1$H NMR (CDCl$_3$, 250 MHz) δ 10.75 (1H, br s, COOH), 7.87 (2H, m, Ar), 7.67 (2H, m, Ar), 7.07 (1H, s, CH═C), 4.09-4.12 (2H, q, CH$_2$CH3), 1.38 (3H, t, J=5 and 7.5 Hz, CH$_2$CH$_3$). Found: C, 66.28: H, 5.12; N, 6.42. Calculated for C$_{12}$H$_{11}$NO$_3$ C, 66.36; H, 5.09; NS, 6.45]. M/z [(Cl) 217 (M)$^+$ 250%, 218 (M+H)$^+$ 200%, 235 (M+NH$_4$)$^+$ 100%.

EXAMPLE 7

(Z)-3-(3-(benzyloxy)-4-methoxyphenyl)-2-ethoxyacrylic Acid

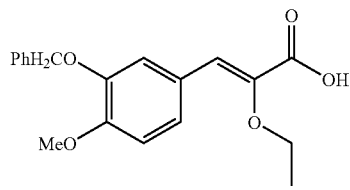

Pink crystalline solid. M.p. 147-148° C. $^1$H NMR (CDCl$_3$, 250 MHz) δ 11.82 (1H, br s, COOH), 7.66 (1H, s CH═C), 7.24-7.57 (8H, m, Ar), 5.17 (2H, s, CH$_2$O), 3.83-3.99 (2H, q, CH$_2$CH$_3$), 3.94 (3H, s, OCH$_3$), 1.22-1.29 (3H, t, CH$_2$CH$_3$). Found: C, 69.40; H, 6.18, Calculated for C$_{19}$H$_{20}$O$_5$; C, 69.51; H, 6.15. M/z [(Cl) 328 (M)$^+$ 20%, 329 (M+H)$^+$ 45%, 346 (M+NH$_4$)$^+$ 100%.

EXAMPLE 8

(Z)-2-ethoxy-3-(3-methoxyphenyl)acrylic Acid

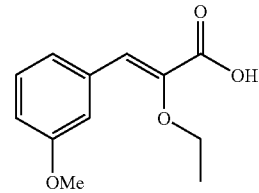

White crystalline solid. M.p. 99-100° C. $^1$H NMR (CDCl$_3$, 250 MHz) δ 12.07 (1H, br s, COOH), 7.56 (1H, br s, Ar), 7.29 (2H, m, Ar), 7.15 (1H, s, CH═C), 6.92 (1H, m, Ar), 4.07 (2H, q, J=7.5 Hz, CH$_2$), 3.83 (3H, s, OCH$_3$), and 1.37 (3H, t, J=7 Hz). Found: C, 65.13; H, 6.37, Calculated for C$_{12}$H$_{14}$O$_4$; C, 64.86; H, 6.35. M/z [(Cl) 222 (M)$^+$ 30%, 223 (M+H)+ 50%, 240 (M+NH$_4$)$^+$ 100%; [Found: 223.09705; required for C$_{12}$H15O$_4$; 223.09155].

EXAMPLE 9

General Hydrogenation Screening Method

Into a 45 ml autoclave was placed ligand (3.25×10$^{-3}$ mM) and the vessel placed under vacuum/Ar cycles. The vessel was then flushed with Argon. A degassed solution of [(COD)$_2$Rh]BF$_4$ in MeOH (5 ml of a 0.64 mM solution) was then added by syringe/needle and a rubber bung placed over the vessel to maintain an inert atmosphere. This mixture was stirred for 10 min to give a clear yellow solution. A degassed solution of starting material in MeOH was then added by syringe/needle while carefully attempting to maintain an inert atmosphere. The autoclave was then connected to a Parr 3000 multi-vessel reactor system and then placed under Ar (5 bar) and vented while stirring, this process was repeated 3 times. After the final vent the mixture was placed under H$_2$ (50 bar)

and again vented carefully. The mixture was then placed under $H_2$ (50 bar), sealed and heated to the desired temperature for the required time. After this time the reaction mixture was cooled and the vessel vented. An aliquot of 0.5-1.0 ml was then taken for analysis.

EXAMPLE 10

(S)-2-(3-(3-methoxypropoxy)-4-methoxybenzyl)-3-methylbutanoic Acid

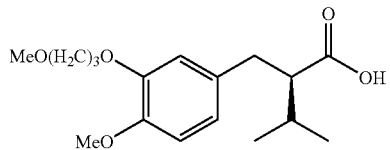

Into a 45 ml autoclave was placed 1,1' bis-[($R_P,S_C,R_{Fe}$) L1 (0.0063 g, 0.0069 mmol), [(COD)$_2$Rh]BF$_4$ (0.0025 g, 0.0061 mmol) and (E)-2-(3-(3-methoxypropoxy)-4-methoxybenzylidene)-3-methylbutanoic acid (2 g, 6.49 mmol). The vessel was then placed under vacuum/Ar cycles. The vessel was then flushed with Argon and a rubber bung placed over the vessel to maintain an inert atmosphere. Degassed MeOH (10 ml) was then added by cannula taking care to maintain an inert atmosphere in the vessel. The vessel was then sealed and stirring commenced. The vessel was then placed under Ar (5 bar) and vented, this process was repeated three times. The autoclave was then placed under $H_2$ (50 bar) and again vented carefully. The mixture was then placed under $H_2$ (50 bar), sealed and heated to 40° C. for 12 h. After this time the reaction mixture was cooled and the vessel vented. An aliquot of 0.5-1.0 ml was then taken for analysis. Conversion >98%, e.e >98.5% (major enantiomer second running peak).

$^1$H NMR (CDCl$_3$, 250.13 MHz): δ 1.01 (m, 6H), 1.95 (m, 1H); 2.05 (m, 2H); 2.45 (m, 1H); 2.78 (m, 2H); 3.35 (s, 3H), 3.55 (m, 2H); 3.83 (s, 3H); 4.10 (m, 2H); 6.65-6.80 (m, 3H).

HPLC Method for e.e. Determination of 2-(3-(3-methoxypropoxy)-4-methoxybenzyl)-3-methylbutanoic Acid Chiralpak-AD column (250 mm×4.6 mm), 94% Hexane, 3% 2-methyl-2-propanol and 3% t-amyl alcohol, flow: 1 ml/min, 230 nm. S-acid 13.15 min (largest peak with bis-[($R_P,S_C,R_{Fe}$)]1), R-acid 14.01 min, starting material 42.73 min.

HPLC Method for e.e. Determination of 2-(3-(3-methoxypropoxy)-4-methoxybenzyl)-3-methylbutanoic Acid (Methyl Ester)-diazomethane Derivatization Into a 10 ml vial was placed a stirring bar and a 1 ml aliquot of the crude hydrogenation reaction mixture. With vigorous stirring trimethylsilyl diazomethane in hexane (2 M) was added drop-wise into the reaction mixture and the good yellow colour of the diazomethane solution disappeared along with good gas evolution. This drop-wise process was continued until the reaction mixture became a yellow colour and gas evolution ceased. Neat acetic acid (15-30 µl, —Caution too much acetic acid and excessive gas evolution occurs) was then added upon which the mixture became very pale yellow. Approximately ⅓ of this mixture was then filtered through a small pad of wetted silica in a Pasteur pipette washing with a little hexane/IPA (80:20). The resulting solution was then analysed using HPLC: Chiralpak-AD column (250 mm×4.6 mm), 95% Hexane, 5% i-Propyl alcohol, flow: 1 ml/min, 230 nm. Product enantiomers; 9-10 min, Starting material; 14-16 min.

Note: the order of elution of the enantiomers is reversed relative to analysis on the non-derivatized acids.

1,1'bis-[($S_P,R_C,S_{Fe}$)]L1 yields (R)-2-(3-(3-methoxypropoxy)-4-methoxybenzyl)-3-methylbutanoic Acid 1,1'bis-[($R_P,S_C,R_{Fe}$)]L1 yields (S)-2-(3-(3-methoxypropoxy)-4-methoxybenzyl)-3-methylbutanoic Acid

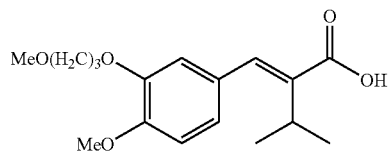

(E)-2-(3-(3-methoxypropoxy)-4-methoxybenzylidene)-3-methylbutanoic Acid

EXAMPLE 11

TABLE 1.0

Results of enantioselective hydrogenations on (E)-2-(3-(3-methoxypropoxy)-4-methoxybenzylidene)-3-methylbutanoic acid with bis-[($S_P,R_C,S_{Fe}$)] L1 at 50 bar $H_2$ pressure.

| entry | s/c ratio | T (° C.) | Substrate [M] | Conversion (%) | e.e. |
|---|---|---|---|---|---|
| 1 | 500:1 | 40 | 0.16 | >95 | 99.6[1] |
| 2 | 500:1 | 50 | 0.16 | >95 | 99.6[2] |
| 3 | 500:1 | 65 | 0.16 | >95 | 99.3[2] |
| 4 | 1000:1 | 40 | 0.55 | 72 | 98.5[3] |
| 5 | 2000:1 | 40 | 0.55 | 72 | 98.3[3] |

[1]Reactions carried out in MeOH for 20 h
[2]Reactions carried out in MeOH for 5 h
[3]Reactions carried out in MeOH for 14 h

EXAMPLE 12

TABLE 2.0

Results of enantioselective hydrogenations on (E)-2-(3-(3-methoxypropoxy)-4-methoxybenzylidene)-3-methylbutanoic acid with bis-[($S_P,R_C,S_{Fe}$)] L1 at 50 bar $H_2$ pressure.

| entry | s/c ratio | T (° C.) | Substrate [M] | Solvent MeOH:1-BuOH | e.e. |
|---|---|---|---|---|---|
| 1 | 1000:1 | 40 | 0.65 | 8.75:1 | 98.7 |
| 2 | 1000:1 | 50 | 0.65 | 8.75:1 | 98.2 |
| 3 | 1000:1 | 65 | 0.65 | 8.75:1 | 96.6 |

EXAMPLE 13

TABLE 3.0

Results of enantioselective hydrogenations on (E)-2-(3-(3-methoxypropoxy)-4-methoxybenzylidene)-3-methylbutanoic acid with bis-[($S_P$,$R_C$,$S_{Fe}$)] L1 at 50 bar $H_2$ pressure (using solid addition method*)

| entry | Time (h) | T (° C.) | Substrate [M] | s/c ratio | e.e. |
|---|---|---|---|---|---|
| 1 | 4 | 50 | 0.55 | 1000:1 | 98.6 |
| 2 | 4 | 60 | 0.55 | 2000:1 | 98.4 |
| 3 | 4 | 60 for 1 h then 50 | 0.55 | 1000:1 | 98.2 |

Note:
in all cases >98% conversion was observed
*All solids (substrate, ligand and metal source) placed in vessel then solvent added

EXAMPLE 14

Ligands containing flexible linker units have been found to be most preferable for the enantioselective hydrogenation of the acid substrates described.

TABLE 4.0

Results of enantioselective hydrogenations on (E)-2-(3-(3-methoxypropoxy)-4-methoxybenzylidene)-3-methylbutanoic acid with ligands L1-L3 at 50 bar $H_2$ pressure in MeOH.

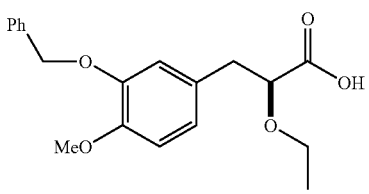

L2

| entry | Ligand | T (° C.) | Time (h) | S/C ratio | Conversion (%) | e.e. (%) |
|---|---|---|---|---|---|---|
| 1 | L1 | 40 | 12 | 1000:1 | 83 | >99 |
| 2 | L2 | 40 | 12 | 1000:1 | 52 | 90.8 |

EXAMPLE 15

HPLC Method for e.e. Determination for (S)-2-ethoxy-3-(thiophen-2-yl)propanoic Acid (as Methyl Ester)

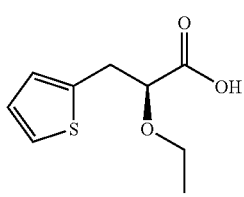

After derivatization:
Chiralpak-AD column (250 mm×4.6 mm), 95% Hexane, 2.5% 2-methyl-2-propanol and 2.5% t-amyl alcohol, flow: 1 ml/min, 236 nm. Enantiomers 5.44 and 5.81 min (largest peak with bis-[($S_P$,$R_C$,$S_{Fe}$)]1).

EXAMPLE 16

HPLC Method for e.e. Determination for (S)-3-(3-(benzyloxy)-4-methoxyphenyl)-2-ethoxypropanoic Acid Chiralpak-AD column (250 mm×4.6 mm), 93% Hexane, 7% i-Propyl alcohol, flow: 1.2 ml/min, 235 nm. Enantiomers 11.71 min, 13.33 min (largest peak with bis-[($R_P$,$S_C$,$R_{Fe}$)]1), starting material 36.68 min.

EXAMPLE 17

TABLE 5.0

Results of enantioselective hydrogenations on (Z)-[-(3-Benzyloxy-4-methoxyphenyl)]-2-ethoxyacrylic acid with bis-[($S_P$,$R_C$,$S_{Fe}$)] 1 at 48 bar $H_2$ pressure for 12 h.

| entry | s/c ratio | T (° C.) | Substrate [M] | e.e. (%) |
|---|---|---|---|---|
| 1 | 2000:1 | 50 | 0.40 | 96.2 |
| 2 | 2000:1 | 50 | 0.83 | 93.4 |
| 3 | 250:1 | 55 | 0.25 | 97.1 |
| 4 | 500:1 | 55 | 0.5 | 97.6 |
| 5 | 1000:1 | 55 | 1.0 | 94.9 |
| 6 | 1500:1 | 55 | 1.5 | 90.9 |
| 7 | 1000:1 | 80 | 1 | 81.2 |

All reactions carried out in MeOH
All reactions achieved >98% conversion

EXAMPLE 18

HPLC Method for e.e. Determination for (S)-2-ethoxy-3-(thiophen-3-yl)propanoic Acid

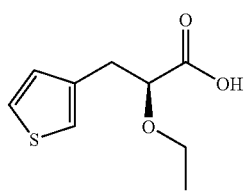

Chiralpak-AD column (250 mm×4.6 mm), 99% Hexane, 1% i-Propyl alcohol, flow: 0.7 ml/min, Integrated 235-239 nm. Enantiomers 9.71 min, 10.88 min (largest peak with bis-[($R_P$,$S_C$,$R_{Fe}$)]1), starting material 16.35 min.

EXAMPLE 19

HPLC Method for e.e. Determination for (S)-2-ethoxy-3-(3-methoxyphenyl)propanoic Acid (as Methyl Ester)

After derivatization:
Chiralpak-AD column (250 mm×4.6 mm), 95% Hexane, 2.5% 2-methyl-2-propanol and 2.5% t-amyl alcohol, flow: 1 ml/min, Integrated 280-290 nm. Enantiomers 7.49 and 10.00 min (largest peak with bis-[($S_P$,$R_C$,$S_{Fe}$)]1).

EXAMPLE 20

TABLE 6.0

Screening results of enantioselective hydrogenations on various (Z)-substituted 3-aryl-2-ethoxyacrylic acid substrates with bis-[($S_P$,$R_C$,$S_{Fe}$)] 1 at 50 bar $H_2$ pressure.

| entry | s/c ratio | T (° C.) | Substrate [M] | Substituted aryl | e.e (%) |
|---|---|---|---|---|---|
| 1 | 500:1 | 40 | 0.41 | 3-OMe | 95.2 |
| 2 | 1000:1 | 40 | 0.82 | 3-OMe | 94.6 |
| 3 | 500:1 | 35 | 0.50 | 4-CN | 98.0 |
| 4 | 500:1 | 55 | 0.50 | 4-CN | 96.5 |
| 5 | 500:1 | 50 | 0.41 | 2-thienyl | 95.0 |
| 6 | 1000:1 | 55 | 0.41 | 3-thienyl | 96.5 |

All reactions carried out in MeOH

The invention claimed is:

1. A metallocene-based phosphine ligand for use in enantioselective catalysis, the ligand having the Formula:

wherein:
M is a metal;
Z is P;
L is a linker;
$R^1$ is selected from substituted and unsubstituted, branched- and straight-chain alkyl, alkoxy, alkylamino, substituted and unsubstituted cycloalkyl, substituted and unsubstituted cycloalkoxy, substituted and unsubstituted cycloalkylamino, substituted and unsubstituted carbocyclic aryl, substituted and unsubstituted carbocyclic aryloxy, substituted and unsubstituted heteroaryl, substituted and unsubstituted heteroaryloxy, substituted and unsubstituted carbocyclic arylamino and substituted and unsubstituted heteroarylamino, wherein the heteroatom is independently selected from sulphur, nitrogen, and oxygen;

X* is selected from:

wherein R, $R^2$ and $R^3$ are independently selected from substituted and unsubstituted, branched- and straight-chain alkyl, substituted and unsubstituted cycloalkyl, substituted and unsubstituted carbocyclic aryl, and substituted and unsubstituted heteroaryl wherein the heteroatom is independently selected from sulphur, nitrogen, or oxygen.

2. A ligand according to claim 1 wherein $R^2$ and $R^3$ form, together with the nitrogen to which they are attached, an optionally substituted hetero-ring.

3. A ligand according to claim 1 which exhibits chirality at phosphorus.

4. A ligand according to claim 3 wherein the chiral configuration of the first phosphorus substituent bound to L is the same as the chiral configuration of the second phosphorus substituent bound to L.

5. A ligand according to claim 1 wherein L is derived from a dianionic reactive species.

6. A ligand according to claim 5 wherein L is selected from metallocenes, diphenyl ethers, xanthenes, 2,3-benzothiophene, 1,2-benzene, cyclic anhydrides or succinimides.

7. A ligand according to claim 6 wherein L is ferrocene.

8. The enantiomer of a ligand according to claim 1.

9. The diastereomer(s) of a ligand according to claim 1.

10. A transition metal complex containing a transition metal coordinated to a ligand according to claim 1.

11. A transition metal complex according to claim 10 wherein the metal is a Group VIB or a Group VIII metal.

12. A transition metal complex according to claim 11 wherein the metal is selected from rhodium, ruthenium, iridium, palladium, platinum or nickel.

13. In a process which comprises conducting enantioselective catalysis in the presence of a catalyst, the improvement wherein the ligand of the catalyst is a ligand according to claim 1.

14. In a process which comprises conducting enantioselective catalysis in the presence of a catalyst, the improvement wherein the catalyst is a transition metal complex according to claim 10.

* * * * *